US012644086B2

(12) United States Patent
Park

(10) Patent No.: US 12,644,086 B2
(45) Date of Patent: Jun. 2, 2026

(54) ROLLED SCAFFOLD FOR LARGE SCALE CELL CULTURE IN MONOLAYER

(71) Applicant: Board of Supervisors of Louisiana State University and Agricultural and Mechanical College, Baton Rouge, LA (US)

(72) Inventor: Kidong Park, Baton Rouge, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 1373 days.

(21) Appl. No.: 16/965,186

(22) PCT Filed: Jan. 25, 2019

(86) PCT No.: PCT/US2019/015063
§ 371 (c)(1),
(2) Date: Jul. 27, 2020

(87) PCT Pub. No.: WO2019/147879
PCT Pub. Date: Aug. 1, 2019

(65) Prior Publication Data
US 2024/0034976 A1 Feb. 1, 2024

Related U.S. Application Data

(60) Provisional application No. 62/621,635, filed on Jan. 25, 2018.

(51) Int. Cl.
*C12M 1/12* (2006.01)
*B32B 27/26* (2006.01)
*B32B 27/28* (2006.01)

(52) U.S. Cl.
CPC ............ *C12M 25/14* (2013.01); *B32B 27/26* (2013.01); *B32B 27/285* (2013.01)

(58) Field of Classification Search
CPC ...... B32B 27/285; B32B 27/26; C12M 23/08; C12M 25/02; C12M 25/14; C12M 23/26
See application file for complete search history.

(56) References Cited

U.S. PATENT DOCUMENTS 3,853,712 A 12/1974 House
4,689,302 A 8/1987 Goldberg
(Continued)

FOREIGN PATENT DOCUMENTS

DE 69633189 8/2005

OTHER PUBLICATIONS

Liu et al. The fabrication and cell culture of three-dimensional rolled scaffolds with complex micro-architectures. Biofabrication (2012), 4, 015004. (Year: 2012).*

(Continued)

*Primary Examiner* — Sean C. Barron
(74) *Attorney, Agent, or Firm* — Baker, Donelson, Bearman, Caldwell & Berkowitz, PC

(57) ABSTRACT

The present invention provides rolled scaffold devices and cell culture systems that can provide a large surface-area-to-volume ratio for expanded cell culture. The rolled scaffolds minimize shear stress on cultured cells and support sufficient and uniform mass transfer rates of gases and nutrients. The rolled scaffolds can be connected to a media source via holders to support large-scale expansion and maintenance of cell cultures.

6 Claims, 10 Drawing Sheets

(56) References Cited

U.S. PATENT DOCUMENTS

| | | | |
|---|---|---|---|
| 5,079,168 | A | 1/1992 | Amiot |
| 5,240,322 | A | 8/1993 | Haber |
| 5,266,476 | A | 11/1993 | Sussman |
| 5,869,329 | A | 2/1999 | Berndt |
| 8,178,345 | B2 | 5/2012 | Bennett |
| 2011/0196660 | A1 | 8/2011 | Liu |
| 2013/0184724 | A1 | 7/2013 | Downes |
| 2014/0306371 | A1 | 10/2014 | Guenther |
| 2018/0116959 | A1 | 5/2018 | Desimone |

OTHER PUBLICATIONS

Ahn, S.H. and Guo, L.J. (2008), High-Speed Roll-to-Roll Nanoimprint Lithography on Flexible Plastic Substrates. Adv. Mater., 20: 2044-2049.

Badenes SM, Fernandes TG, Cordeiro CSM, Boucher S, Kuninger D, Vemuri MC, et al. (2016) Defined Essential 8™ Medium and Vitronectin Efficiently Support Scalable Xeno-Free Expansion of Human Induced Pluripotent Stem Cells in Stirred Microcarrier Culture Systems. PLoS One 11(3): e0151264.

Bauwens C et al., Biotechnology and Bioengineering, 2005, 90(4):452-461.

Cioffi M et al., Journal of biomechanics, 2008, 41(14):2918-2925.

Jaymi T. Cormier, Nicole I. Zur Nieden, Derrick E. Rancourt, and Michael S. Kallos. Tissue Engineering.Nov. 2006.3233-3245.

Croughan MS et al., Biotechnology and bioengineering, 1987, 29(1):130-141.

Cui X, Zhang X, Guan X, et al. Shear stress augments the endothelial cell differentiation marker expression in late EPCs by upregulating integrins. Biochemical and Biophysical Research Communications. Aug. 2012;425(2):419-425.

Eibes G et al., Journal of biotechnology, 2010, 146(4):194-197.

Grein TA et al., Process Biochemistry, 2016, 51(9):1109-1119.

Gupta P et al., Cytotechnology, 2016, 68(1):45-59.

Hu AY, Weng TC, Tseng YF, et al. Microcarrier-based MDCK cell culture system for the production of influenza H5N1 vaccines. Vaccine. Oct. 2008;26(45):5736-5740.

Jing D et al., Cell transplantation, 2010, 19(11):1397-1412.

Kehoe DE et al., Tissue Engineering Part A, 2009, 16(2):405-421.

Kooy, N., Mohamed, K., Pin, L.T. et al. A review of roll-to-roll nanoimprint lithography. Nanoscale Res Lett 9, 320 (2014).

Ku K et al., Biotechnology and Bioengineering, 1981, 23(1):79-95.

Leung HW et al., Tissue Engineering Part C: Methods, 2010, 17(2):165-172.

Liu YL et al., Biotechniques, 2003, 34(1):184-189.

Looby, D.; Griffiths, J.B.: Fixed bed porous glass sphere bioreactors for animal cells. Cytotechnology 1 (1988) 339-346.

Martens DE et al., Cytotechnology, 1996, 21(1):45-59.

Meuwly F et al., Biotechnology and bioengineering, 2006, 93(4):791-800.

Nam JH et al., Biotechnology progress, 2007, 23(3):652-660.

Ng, Y & Berry, J & Butler, Michael. (1996). Optimization of physical parameters for cell attachment and growth on macroporous microcarriers. Biotechnology and bioengineering. 50. 627-35.

Nilsson K et al., Nature Biotechnology, 1986, 4(11):989-990.

O'Connor KC et al., Biotechnology techniques, 1992, 6(4):323-328.

Odeleye Aoo et al., Chemical engineering science, 2014, 111:299-312.

Petti SA et al., Biotechnology progress, 1994, 10(5):548-550.

Preissmann A et al., Cytotechnology, 1997, 24(2):121-134.

Santiago PA et al., Process biochemistry, 2011, 46(1):35-45.

Schulz et al., 2004 Stem Cells, 22(7):1218-38.

Sucosky P et al., Biotechnology and bioengineering, 2004, 85(1):34-46.

Trummer E et al., Biotechnology and bioengineering, 2006, 94(6):1033-1044.

Wang Y, Chou BK, Dowey S, He C, Gerecht S, Cheng L. Scalable expansion of human induced pluripotent stem cells in the defined xeno-free E8 medium under adherent and suspension culture conditions. Stem Cell Res. Nov. 2013;11(3):1103-16.

Wolfe, R.P. and Ahsan, T. (2013), Shear stress during early embryonic stem cell differentiation promotes hematopoietic and endothelial phenotypes. Biotechnol. Bioeng., 110: 1231-1242.

Xing Z et al., Biotechnology and bioengineering, 2009, 103(4):733-746.

Yamamoto K, Sokabe T, Watabe T, Miyazono K, Yamashita JK, Obi S, Ohura N, Matsushita A, Kamiya A, Ando J. Fluid shear stress induces differentiation of Flk-1-positive embryonic stem cells into vascular endothelial cells in vitro. Am J Physiol Heart Circ Physiol. Apr. 2005;288(4):H1915-24.

Youn, B.S., Sen, A., Kallos, M.S., Behie, L.A., Girgis-Gabardo, A., Kurpios, N., Barcelon, M. and Hassell, J.A. (2005), Large-Scale Expansion of Mammary Epithelial Stem Cell Aggregates in Suspension Bioreactors. Biotechnol Progress, 21: 984-993.

International Search Report and Written Opinion issued in App. No. PCT/US2019/015063, mailing date Oct. 25, 2019, 12 pages.

Extended European Search Report issued in App. No. EP19743914. 4, dated Sep. 22, 2021, 14 pages.

Otto-Wilhelm Merten, "Advances in cell culture: anchorage dependence", Phil. Trans. R. Soc. B., 370, 20140040.

European Patent Office Communication pursuant to Rules 70(2) and 70a(2) EPC issued in App. No. EP19743914.4, dated Oct. 12, 2021, 1 page.

Adams, W.J. et al. The FASEB Journal, Supplement 27(1):379.1 (2013). Experimental Biology 2013 Meeting Abstracts: The FASEB Journal: vol. 27, No. S1 (wiley.com).

Cormier, J.T. et al. Expansion of undifferentiated murine embryonic stem cells as aggregates in suspension culture bioreactors. Tissue engineering, 12(11):3233-3245 (2006).

Keller, J. et al. A Fluidized Bed Reactor for the Cultivation of Animal Cells. In: Galindo, E., Ramírez, O.T. (eds) Advances in Bioprocess Engineering. Springer, Dordrecht, pp. 115-121 (1994).

Lu, H. et al. Microfluidic shear devices for quantitative analysis of cell adhesion. Analytical chemistry, 76 (18):5257-5264 (2004).

* cited by examiner

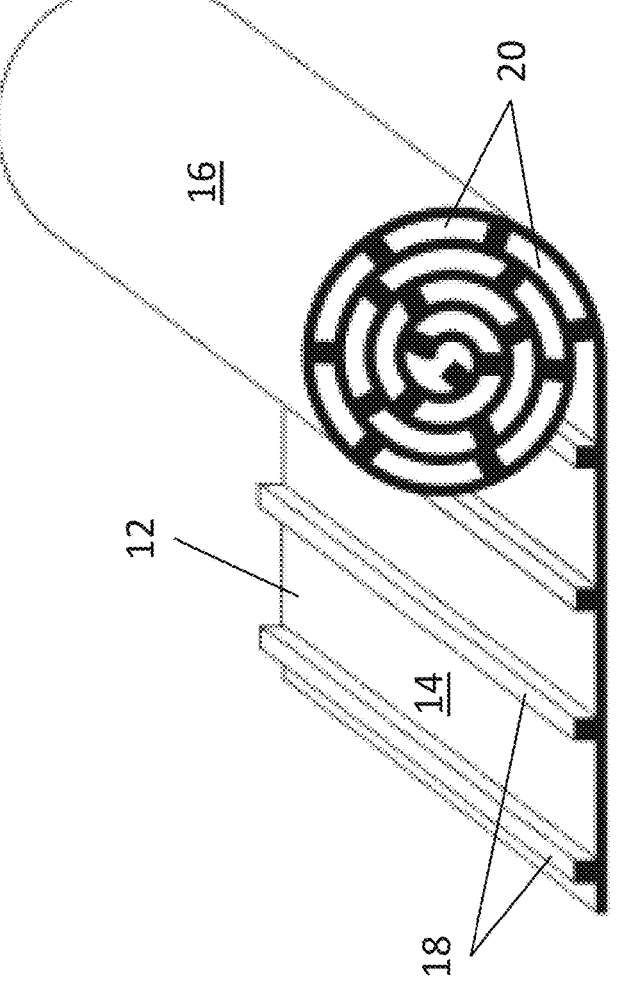
Figure 1

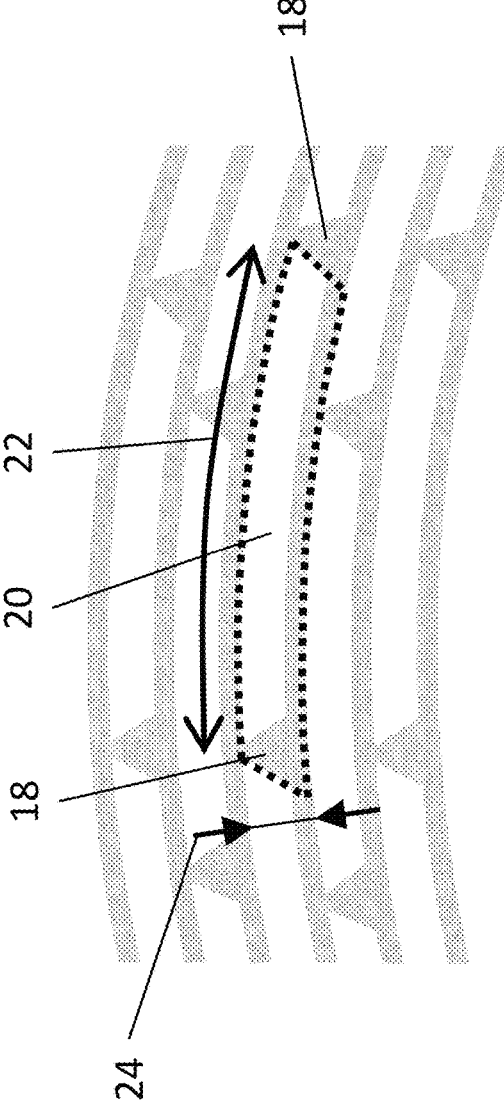
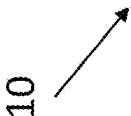
Figure 2

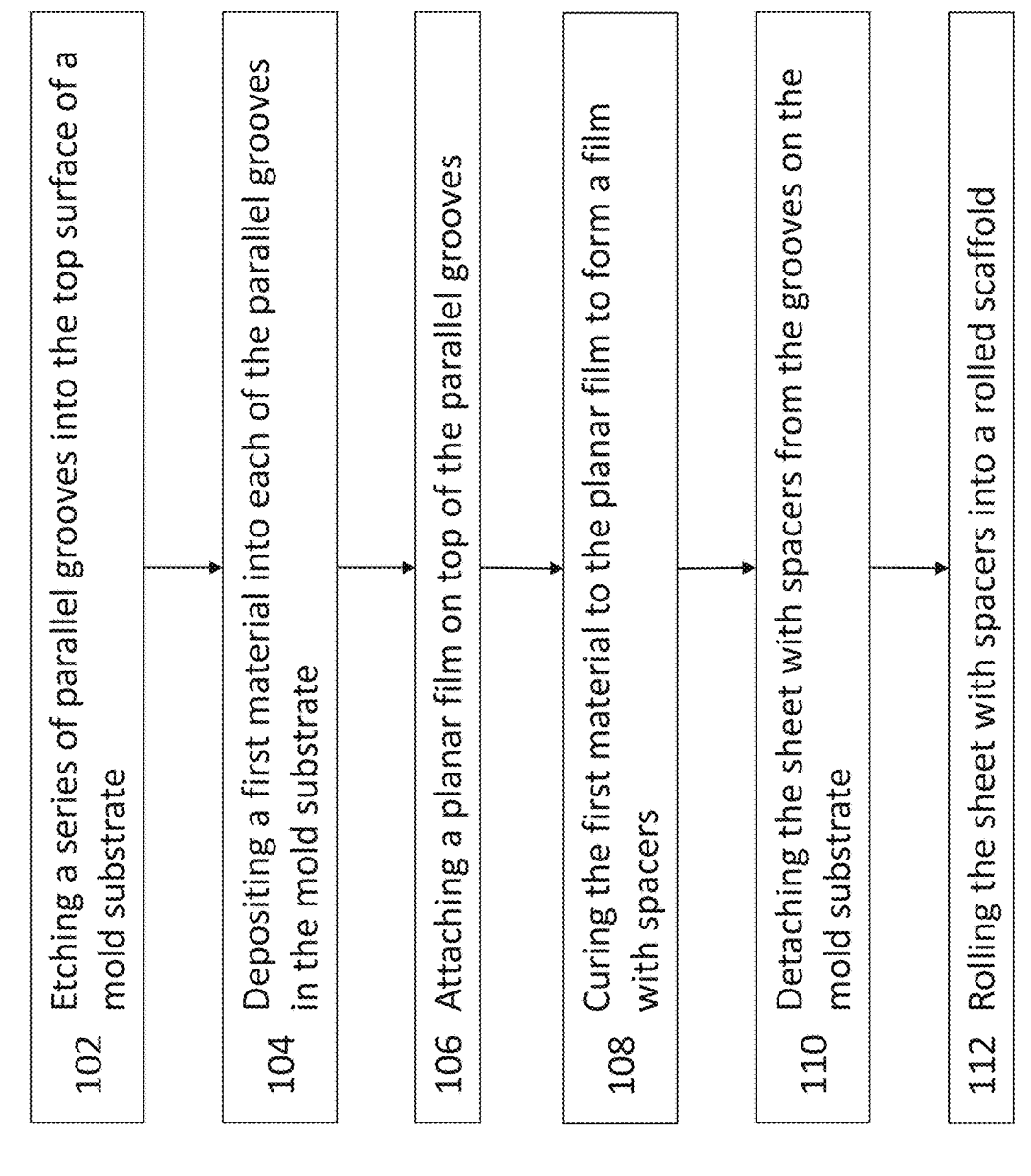

100

102   Etching a series of parallel grooves into the top surface of a mold substrate 104   Depositing a first material into each of the parallel grooves in the mold substrate 106   Attaching a planar film on top of the parallel grooves 108   Curing the first material to the planar film to form a film with spacers 110   Detaching the sheet with spacers from the grooves on the mold substrate 112   Rolling the sheet with spacers into a rolled scaffold

Figure 5

ROLLED SCAFFOLD FOR LARGE SCALE CELL CULTURE IN MONOLAYER

CROSS-REFERENCE TO RELATED APPLICATIONS

This application is a 35 U.S.C. § 371 national phase application from, and claiming priority to, International Application No. PCT/US2019/015063, filed Jan. 25, 2019, which claims priority to U.S. Provisional Patent Application No. 62/621,635, filed Jan. 25, 2018, the contents both of which are incorporated by reference herein in its their entirety.

BACKGROUND OF THE INVENTION

In laboratories, adherent cells are typically cultured with culture flasks having culture areas of between 25 and 175 cm². However, large-scale cell expansion often requires over hundreds or thousands of such culture flasks, which is impractical due to the amount of required labor and space. Roller bottles (Liu Y L et al., Biotechniques, 2003, 34(1): 184-189) or multilayer planar vessels (U.S. Pat. No. 8,178, 345) can be used to provide much larger growth areas of between about 1,000 and 10,000 cm². Using these alternatives to expand cells tends to be an easy and more direct translation from culture flasks, but they are still limited in their scale-up potential.

Currently, for large scale culture of adherent cells, a number of different platforms are available, such as micro-carrier-based stirred bioreactors (Eibes G et al., Journal of biotechnology, 2010, 146(4):194-197; Hu A Y-C et al., Vaccine, 2008, 26(45):5736-5740; Lundgren B et al., Bio-separation and Bioprocessing: Biochromatography, Membrane Separations, Modeling, Validation, 1998, 165-222; Nam J H et al., Biotechnology progress, 2007, 23(3):652-660), packed-bed bioreactors (Looby D et al., Cytotechnology, 1988, 1(4):339-346), fluidized-bed bioreactors (Keller J et al., Advances in Bioprocess Engineering, 1994, 115-121), and hollow fiber bioreactors (Ku K et al., Biotechnology and Bioengineering, 1981, 23(1):79-95). Among these, the microcarrier-based stirred bioreactors are widely used to culture cells that cannot survive as single cells or cell aggregates. Anchorage dependent cells are grown on outer surfaces of suspended microcarriers, which are essentially solid microspheres. The microcarrier-based stirred bioreactors can support large capacity and massive quantities of anchorage dependent cells can be produced in a single run.

As the capacity of a bioreactor increases, the surface-area-to-volume ratio of the cell suspension decreases. More vigorous stirring and aeration are necessary to maintain mass transfer rate of nutrients and gases for larger numbers of cells (Xing Z et al., Biotechnology and bioengineering, 2009, 103(4):733-746). However, this increases hydrodynamic shear stress, which can produce adverse effects on cells, such as reduced proliferation, low viability, and uncontrolled differentiation of stem cells (Croughan M S et al., Biotechnology and bioengineering, 1987, 29(1):130-141; Gupta Petal., Cytotechnology, 2016, 68(1):45-59; Leung H W et al., Tissue Engineering Part C: Methods, 2010, 17(2): 165-172; Ng Y-C et al., Biotechnology and bioengineering, 1996, O'Connor K C et al., Biotechnology techniques, 1992, 6(4):323-328). The trade-off between the mass transfer rate and the hydrodynamic shear stress makes large-scale expansion of shear-sensitive cells unreliable and leads to timeconsuming optimization of operating conditions on each expansion stage, as those factors are typically affected by the bioreactor's capacity.

One of the approaches to address this issue is to optimize configuration and geometry of stirred bioreactors and their impellers for maximum media mixing and minimum hydrodynamic shear stress. Numerous studies were able to make improvements to a certain degree, yet they could not overcome the fundamental limit imposed by the finite diffusion rate of gases and nutrients and the hydrodynamics (Trummer E et al., Biotechnology and bioengineering, 2006, 94(6): 1033-1044; Odeleye A O O et al., Chemical engineering science, 2014, 111:299-312; Cioffi M et al., Journal of biomechanics, 2008, 41(14):2918-2925; Sucosky P et al., Biotechnology and bioengineering, 2004, 85(1):34-46; Santiago P A et al., Process biochemistry, 2011, 46(1):35-45; Grein T A et al., Process Biochemistry, 2016, 51(9):1109-1119). Another approach is to locally shield cells from the hydrodynamic shear stress. This approach includes macroporous microcarriers (Ng Y-C et al., Biotechnology and bioengineering, 1996, 50(6):627-635, Nilsson K et al., Nature Biotechnology, 1986, 4(11):989-990), fiber discs in packed-bed reactors (Meuwly F et al., Biotechnology and bioengineering, 2006, 93(4):791-800; Petti S A et al., Biotechnology progress, 1994, 10(5):548-550), and various encapsulation methods (Bauwens C et al., Biotechnology and Bioengineering, 2005, 90(4):452-461; Jing D et al., Cell transplantation, 2010, 19(11):1397-1412). Generally, in these techniques, cells are placed inside microstructures to be protected from the hydrodynamic shear stress (Martens D E et al., Cytotechnology, 1996, 21(1):45-59). However, such protection makes it difficult for nutrients and gases to be uniformly available to the cells, as some of them are located deep inside the protective microstructures (Preissmann A et al., Cytotechnology, 1997, 24(2):121-134). For the very same reason, harvesting the cells is very challenging.

Therefore, there is a need for improved devices and systems that are capable of large-scale culturing of adherent cells. The present invention addresses this need.

SUMMARY OF THE INVENTION

In one aspect, the present invention relates to a rolled scaffold comprising: a substantially planar film having an upper surface, a lower surface, a length, and a width; and a plurality of elongate spacers attached to one of the surfaces, the spacers having a height, a width, and a length that spans the entire width of the film; wherein the film is rollable along its length into a cylindrical shape such that the spacers face press against the opposing surface of the rolled film, and wherein the height of the spacers maintain a space between the rolled film layers.

In one embodiment, the spacers have a cross-sectional shape selected from the group consisting of: a square, a rectangle, a trapezoid, a hexagon, a triangle, a circle segment, an ovoid segment, or other similar shapes. In one embodiment, the spacers have one or more discontinuities.

In another aspect, the present invention relates to a rolled scaffold holder comprising a casing having a hollow interior sized to fit the one or more rolled scaffolds of the present invention, wherein the casing comprises a plurality of ports fluidically connected to the hollow interior capable of passing at least one fluid through the rolled scaffold. In one embodiment, the casing is formed from a first and a second endcap connectable at a junction. In one embodiment, the junction is selected from the group consisting of: mated threads, a friction fit, a tab and slot, an adhesive, external clamps, and other methods.

In another aspect, the present invention relates to a method of culturing cells, the method comprising the steps of: attaching at least one cell to at least one surface of the rolled scaffold of the present invention; and administering nutrients and oxygen to the at least one cell by applying a flow of culture media through the rolled scaffold along its length.

In another aspect, the present invention relates to a method of fabricating rolled scaffolds, the method comprising the steps of: etching a series of parallel grooves into the top surface of a mold substrate; depositing a first material into each of the parallel grooves in the mold substrate; attaching a planar film on top of the parallel grooves; curing the first material to the planar film to form a film with spacers; detaching the film with spacers from the grooves on the mold substrate; and rolling the film with spacers into a rolled scaffold.

In one embodiment, the mold substrate is silicone rubber. In one embodiment, the first material is UV-curable resin. In one embodiment, the second material is polyethylene terephthalate. In one embodiment, the mold substrate is attached to a roll and the film is processed continuously and simultaneously in a roll-to-roll process.

In another aspect, the present invention relates to a method of fabricating rolled scaffolds, the method comprising the steps of: providing a planar film having a length and a width; depositing a first material onto the film, the first material being deposited in the form of a plurality of continuous or discontinuous thin lines spanning a portion or an entire width of the film; curing or solidifying the first material to the planar film to form a film with spacers; and rolling the film with spacers into a rolled scaffold. In one embodiment, the first material is melted plastic extruded by a nozzle or multiple nozzles. In one embodiment, the first material is UV-curable resin. In one embodiment, the second material is polyethylene terephthalate. In one embodiment, the first material is continuously deposited onto the film and the film is continuously and simultaneously processed in a roll-to-roll process.

In another aspect, the present invention relates to a cell culturing system, comprising: one or more rolled scaffolds, each comprising a film having an upper surface, a lower surface, and a plurality of elongate spacers attached to one of the surfaces, the film rolled into a cylindrical shape such that the spacers face and press against the opposing surface of the rolled film to maintain a space between the rolled film layers; one or more rolled scaffold holders, each comprising a casing having a hollow interior sized to fit one or more rolled scaffolds, the casing comprises a plurality of ports fluidically connected to the hollow interior capable of passing at least one fluid through the rolled scaffold; one or more media reservoirs; tubing fluidically connecting the media reservoir to each of the rolled scaffold holders; and one or more pumps connected to the tubing.

In one embodiment, the one or more media reservoirs are fluidically connected to one or more media sources, gas sources, chemical reagents, or combinations thereof. In one embodiment, the tubing comprises one or more access ports upstream from the rolled scaffold holders, downstream from the rolled scaffold holders, or both. In one embodiment, the tubing comprises one or more sensors upstream from the rolled scaffold holders, downstream from the rolled scaffold holders, or both. In one embodiment, the one or more sensors are selected from the group consisting of: temperature sensors, flow sensors, pH sensors, gas concentration sensors, glucose sensors, and analyte sensors. In one embodiment, the tubing comprises one or more stopcocks or valves capable of stopping or diverting flow of fluid within the system. In one embodiment, the one or more rolled scaffolds, each within a rolled scaffold holder, are connected to the media reservoir in series, in parallel, or combinations thereof.

In another aspect, the present invention relates to a method of culturing cells, the method comprising the steps of: providing the cell culture system of the present invention; applying a flow of a suspension of cells into one or more rolled scaffold holders, each of the rolled scaffold holders holding one or more rolled scaffolds; stopping the flow such that the suspension of cells attach to at least one surface of each of the rolled scaffolds; applying a flow of culture media through each of the rolled scaffolds to administer nutrients and oxygen to the cells for the cells' growth and metabolism; applying a flow of cell dissociation media through each of the rolled scaffolds such that attached cells are detached from each of the rolled scaffolds; and harvesting detached cells from the flow of cell dissociation media.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

FIG. 1 depicts an exemplary rolled scaffold.

FIG. 2 depicts a cross-section view of an exemplary rolled scaffold having triangular spacers.

FIG. 4A depicts the compartments of a rolled scaffold lined with an adherent cell layer. FIG. 4B depicts the compartments of a rolled scaffold having square spacers.

FIG. 5 is a flowchart of an exemplary method of fabricating rolled scaffolds.

(FIG. 8A) An image of laser-engraved 2D silicone molds for making rolled scaffolds. (FIG. 8B) SEM of the PET film with molded spacers. (FIG. 8C) Phase contrast image of human colon cancer cells (HT29) growing on the PET film between the spacers. (FIG. 8D) Cross-section of the rolled scaffold after rolling. (FIG. 8E) Medium and small rolled scaffold holders shown next to a T-25 flask for size comparison. Medium and small rolled scaffolds have surface areas equivalent to 137 and 17 T-25 flasks, respectively.

FIG. 9A shows the fluidic connection of the rolled scaffold platform. The upstream access port can be used to inject cell suspensions for cell seeding and cell dissociation reagent for cell harvesting. The downstream access port can be used to collect harvested cells. (FIG. 9B) The cell culture system can fit entirely within a $CO_2$ incubator.

(FIG. 10A) The oxygen consumption rate of CHO cells in a medium rolled scaffold. (FIG. 10B) The oxygen consumption rate of CHO cells in a small rolled scaffold. The oxygen consumption rate increases exponentially, indicating active proliferation of CHO cells (Y-axis in log scale). The numbers in the boxes are the number of cells at the end of the culture period.

DETAILED DESCRIPTION

Figure 3:
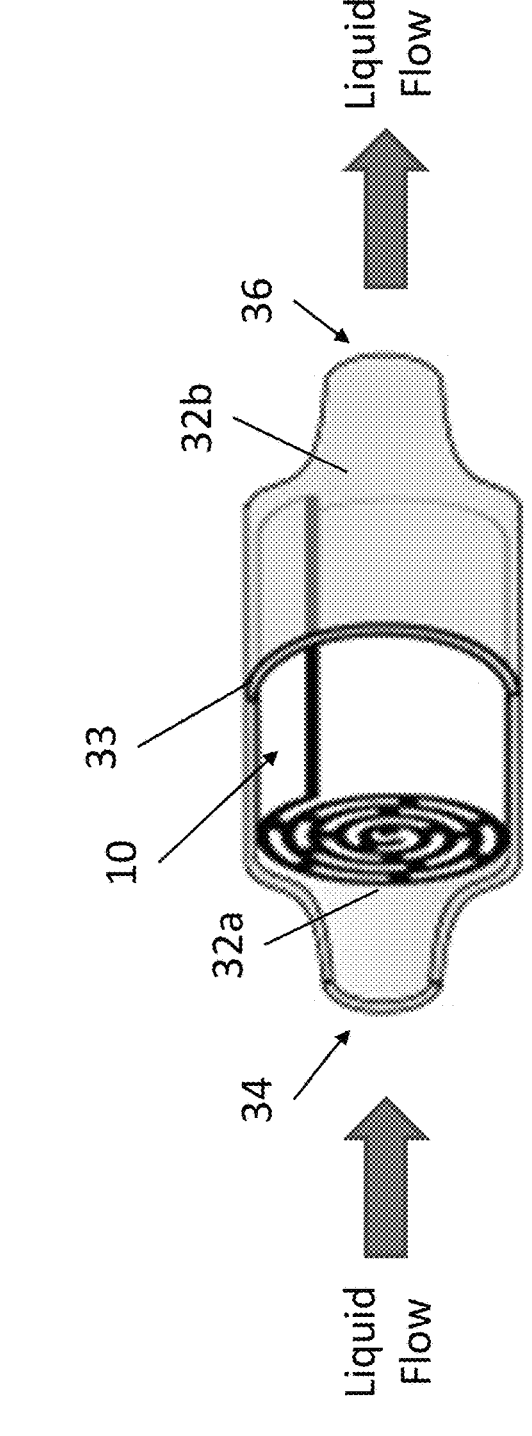
FIG. 3 depicts a partial cutaway view of an exemplary rolled scaffold placed within a holder.

The present invention provides rolled scaffold devices and cell culture systems that can provide a large surface-area-to-volume ratio for expanded cell culture. The rolled scaffolds minimize shear stress on cultured cells and support sufficient and uniform mass transfer rates of gases and nutrients. The rolled scaffolds can be connected to a media source via holders to support large-scale expansion and maintenance of cell cultures.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

"Differentiated" is used herein to refer to a cell that has achieved a terminal state of maturation such that the cell has developed fully and demonstrates biological specialization and/or adaptation to a specific environment and/or function. Typically, a differentiated cell is characterized by expression of genes that encode differentiation associated proteins in that cell. When a cell is said to be "differentiating," as that term is used herein, the cell is in the process of being differentiated.

"Differentiation medium" is used herein to refer to a cell growth medium comprising an additive or a lack of an additive such that a stem cell, adipose derived adult stromal cell or other such progenitor cell, that is not fully differentiated when incubated in the medium, develops into a cell with some or all of the characteristics of a differentiated cell.

The term "derived from" is used herein to mean to originate from a specified source.

"Expandability" is used herein to refer to the capacity of a cell to proliferate, for example, to expand in number or in the case of a cell population to undergo population doublings.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

As used herein "growth factors" is intended the following non-limiting factors including, but not limited to, growth hormone, erythropoietin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor (EGF), fibroblast growth factor (FGF), nerve growth factor, ciliary neurotrophic factor, platelet derived growth factor (PDGF), transforming growth factor (TGF-beta), hepatocyte growth factor (HGF), and bone morphogenetic protein at concentrations of between picogram/ml to milligram/ml levels.

As used herein, the term "growth medium" is meant to refer to a culture medium that promotes growth of cells. A growth medium will generally contain animal serum. In some instances, the growth medium may not contain animal serum.

An "isolated cell" refers to a cell which has been separated from other components and/or cells which naturally accompany the isolated cell in a tissue or mammal.

As used herein, the term "multipotential" or "multipotentiality" is meant to refer to the capability of a stem cell to differentiate into more than one type of cell.

As used herein, a "pluripotent cell" defines a less differentiated cell that can give rise to at least two distinct (genotypically and/or phenotypically) further differentiated progeny cells.

The terms "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew itself or to produce progeny cells which will differentiate into the desired cell type. Unlike pluripotent stem cells, lineage-committed progenitor cells are generally considered to be incapable of giving rise to numerous cell types that phenotypically differ from each other. Instead, progenitor cells give rise to one or possibly two lineage-committed cell types.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

"Progression of or through the cell cycle" is used herein to refer to the process by which a cell prepares for and/or enters mitosis and/or meiosis. Progression through the cell cycle includes progression through the G1 phase, the S phase, the G2 phase, and the M-phase.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, "tissue engineering" refers to the process of generating tissues ex vivo for use in tissue replacement or reconstruction. Tissue engineering is an example of "regenerative medicine," which encompasses approaches to the repair or replacement of tissues and organs by incorporation of cells, gene or other biological building blocks, along with bioengineered materials and technologies.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

Rolled Scaffold

The rolled scaffold is a structure that can culture large populations of cells with adherent culture. The rolled scaffold is unique in that its internal structure is fully defined and engineered for large cell culture density and favorable growth conditions for the cells.

Referring now to FIG. 1, an exemplary rolled scaffold 10 is depicted. Rolled scaffold 10 comprises film 12 having an upper surface 14, a lower surface 16, and a plurality of spacers 18. Film 12 has a substantially planar shape having a length, a width, and a thickness of any suitable size. For example, film 12 can have a length between about 10 cm and 100 m or more, a width between about 1 to 100 cm or more, and a thickness between about 0.01 to 1 mm or more. Film 12 can be constructed from any suitably flexible material, such as a plastic, a polymer, a paper, or a metal. In some embodiments, film 12 is constructed from polyethylene terephthalate. In some embodiments, film 12 is constructed from a material capable of withstanding common sterilization techniques, such as autoclaving, gamma ray sterilization, electron beam sterilization, and the application of any sterilizing gas or solution such as ethylene oxide, chlorine dioxide, and hydrogen peroxide.

Spacers 18 are substantially rigid structures attached to upper surface 14 and extend over the entire width of film 12. In some embodiments, spacers 18 are positioned in parallel over the entire width of film 12. In other embodiments, spacers 18 can be positioned in parallel at an angle over the width of film 12, or in any desired pattern over the width of film 12. Spacers 18 can be provided in a continuous line over the width of film 12, or can be provided as a series of segments over the width of film 12, such as in a dashed line with one or more spaces between each segment. Spacers 18 can have any suitable height and width, such as a height between about 0.01 and 1 mm and a width between about 0.01 and 1 cm. Spacers 18 can have any suitable cross-sectional shape, such as a square, rectangle, trapezoid, hexagon, triangle, circle segment, ovoid segment, and the like. Spacers 18 can be constructed from any suitable material, such as a plastic, a polymer, a resin, or a metal. In some embodiments, spacers 18 are constructed from the same material as film 12. In some embodiments, spacers 18 are constructed from a UV light-curable resin or thermoplastic. In some embodiments, spacers 18 are constructed from a material capable of withstanding common sterilization techniques, such as autoclaving, gamma ray sterilization, electron beam sterilization, and the application of any sterilizing gas or solution such as ethylene oxide, chlorine dioxide, and hydrogen peroxide.

Film 12 can be rolled into the cylindrical shape to form rolled scaffold 10, whereupon the width of film 12 becomes the height of rolled scaffold 10, and the rolled length of film 12 can be described as a radius or diameter of rolled scaffold 10. For example, the rolled scaffold 10 can have a height between about 1 and 100 cm or more, and a radius between about 0.5 cm to 2 m or more. Film 12 can be rolled such that spacers 18 face inwards or outwards. In both rolled configurations, spacers 18 face and press against lower surface 16 and maintain a column of space between upper surface 14 and lower surface 16 to form a plurality of channels 20. Referring now to FIG. 2, a magnified view of channels 20 is depicted. Channel 20 has a width 22 and a height 24. Width 22 can be any suitable distance, such as a width between 0.1 and 5 cm. Height 24 is defined by the height of spacers 18.

The unique geometry of the rolled scaffold provides inherent advantages over conventional large-scale cell culture platforms, which pose the rolled scaffold as a promising biomanufacturing platform for stem cell therapy and biopharmaceutical industries. The rolled scaffold provides a larger surface area than other cell culture platforms, enabling more efficient cell expansion. For example, a rolled scaffold with an exemplary channel width of 1 mm and channel height of 0.1 mm is able to accommodate the growth of cells on both sides of the film; with 0.1 mm of the width being taken up by the spacers, one layer of the film and the spacers can provide a cell culture area that is 2×0.9=1.8 times larger than the unit area of the film. An exemplary layer that is 0.15 mm high with 50 μm thick film and 100 μm high spacers has a surface-area-to-volume ratio of (L×1.8×1 mm)/(L×0.15 mm×1 mm), which is 120 cm$^2$/mL, with L, the length of a rolled scaffold, being 4 cm. Exemplary dimensions of completed rolled scaffolds are presented in Table 1. For a larger capacity, the dimensions of the rolled scaffold can be increased further.

TABLE 1

| Exemplary rolled scaffold sizes and dimensions. (Width, height, and spacing of the spacers are 0.1 mm, 0.1 mm, and 0.9 mm, respectively). | | | | | |
|---|---|---|---|---|---|
| Size | Radius | Internal surface area | Equivalent # of T-25 flask | Internal volume | Max # of cells |
| S | 0.5 cm | 427 cm$^2$ | 17 | 3.1 mL | 42 million |
| M | 1.5 cm | 3,425 cm$^2$ | 137 | 25 mL | 342 million |
| L | 4.5 cm | 30,622 cm$^2$ | 1225 | 229 mL | 3.1 billion |

A large-sized rolled scaffold with a radius of 4.5 cm and a length of 4 cm can provide an internal surface area of 30,622 cm$^2$, equivalent to 1,225 T-25 culture flasks or 3,402 wells on a 6-well plate. The area-to-volume ratio of the rolled scaffold (120 cm$^2$/mL) is equal to or higher than microcarrier bioreactors (GE Cytodex-1, 8-80 cm$^2$/mL), parallel plate flasks (Corning Cell Cube System, 14 cm$^2$/mL), and fiber-disk fixed bed bioreactors (Fibra-cell disk, 120 cm$^2$/mL).

The present invention also relates to rolled scaffold holders. Referring now to FIG. 3, an exemplary holder 30 is depicted. Holder 30 comprises a first endcap 32a and a second endcap 32b connectable to each other at a junction 33 to form a single casing having a hollow interior sized to fit a rolled scaffold 10. Junction 33 can include any suitable means of joining two structures, including mated threads, a friction fit, a tab and slot, an adhesive, external clamps, and the like. In some embodiments, junction 33 is watertight, such as by having near zero clearance in junction 33, or by providing an additional element to prevent leaking, such as with a rubber O-ring or a grease or paste. Holder 30 further comprises an inlet port 34 and an outlet port 36, each fluidically connected to the hollow interior of first endcap 32a and second endcap 32b, respectively. Inlet port 34 and outlet port 36 can each be compatible with any suitable standard for piping and tubing, such as a luer lock system. Holder 30 can be constructed from any suitable material, such as a plastic, a polymer, or a metal. In some embodiments, holder is constructed from a material capable of withstanding common sterilization techniques, such as autoclaving, gamma ray sterilization, electron beam sterilization, and the application of any sterilizing gas or solution such as ethylene oxide, chlorine dioxide, and hydrogen peroxide.

Figure 4B:
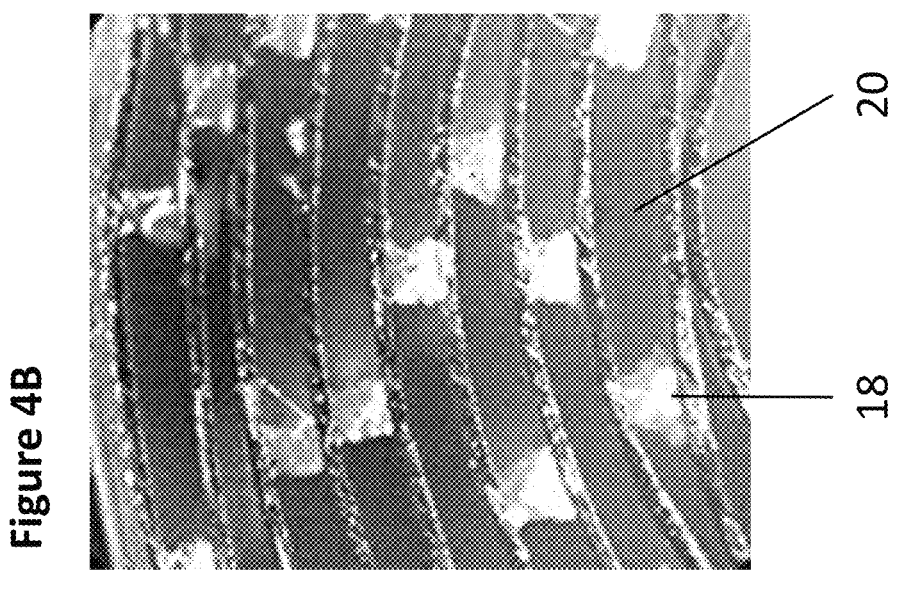
FIG. 4A and FIG. 4B depict various cross-section views of an exemplary rolled scaffold.
Figure 4A:
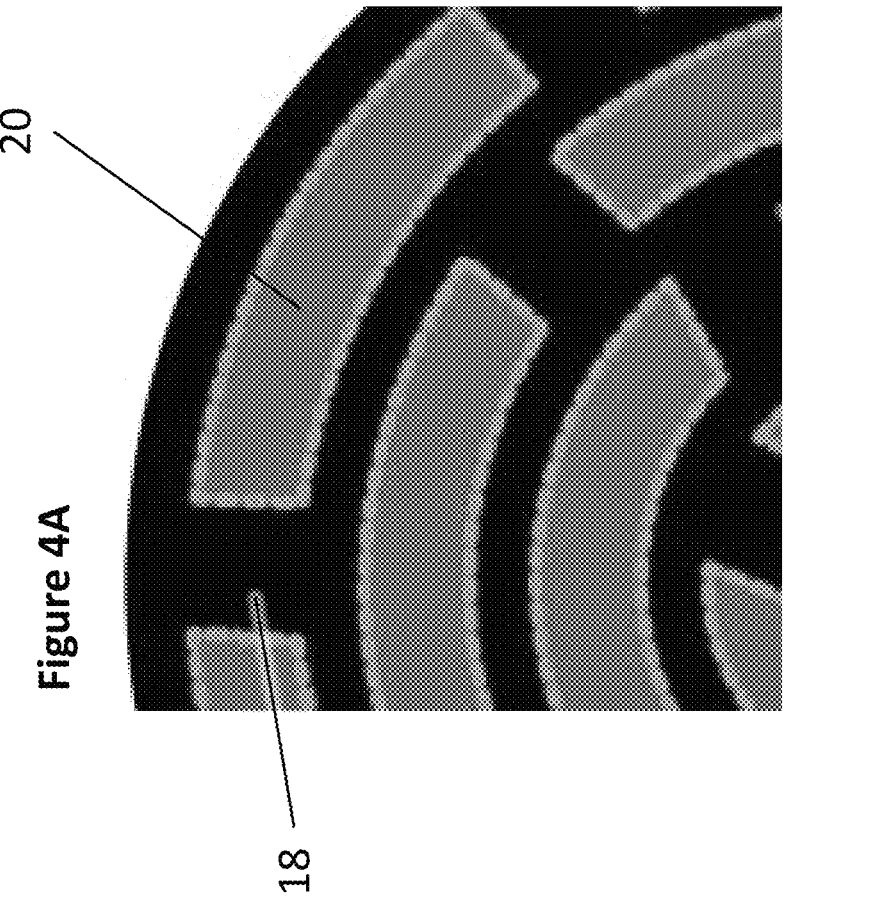

Referring now to FIG. 4A and FIG. 4B, various cross-sectional views of an exemplary rolled scaffold are depicted. In FIG. 4A, cells are shown growing on the inner surface of channels 20. Growth media flowing lengthwise through channels 20 enable the continuous delivery of nutrients and oxygen to adhered cells. In FIG. 4B, compartments of an exemplary rolled scaffold are depicted having square spacers 18.

The rolled scaffold is highly unique in that its microarchitecture is fully defined and engineered for optimal transport of oxygen and nutrients, while it can achieve higher culture capacity than other culture platforms. Unlike stirred bioreactors for suspension culture, which rely on diffusion and turbulent flow for mass transport, the rolled scaffold-based cell biomanufacturing platform transports nutrients and oxygen via convection and laminar flow with much higher efficiency, so that hydrodynamic shear stress is drastically reduced compared to stirred bioreactors. As the geometry of channels in the rolled scaffolds is fully defined, hydrodynamic shear stress and mass transfer rate of nutrients and oxygen are highly uniform and can be precisely controlled, substantially increasing uniformity and reliability of biomanufacturing of therapeutic cells, including stem cells from various sources, protein therapeutics, antibodies, and any other biomolecules produced by cells. Furthermore, the microenvironment of the rolled scaffold is independent of the culture capacity, as the culture capacity is increased by adding more channels without modifying the geometry of the channels.

Methods of Fabricating the Rolled Scaffold

Figure 6:
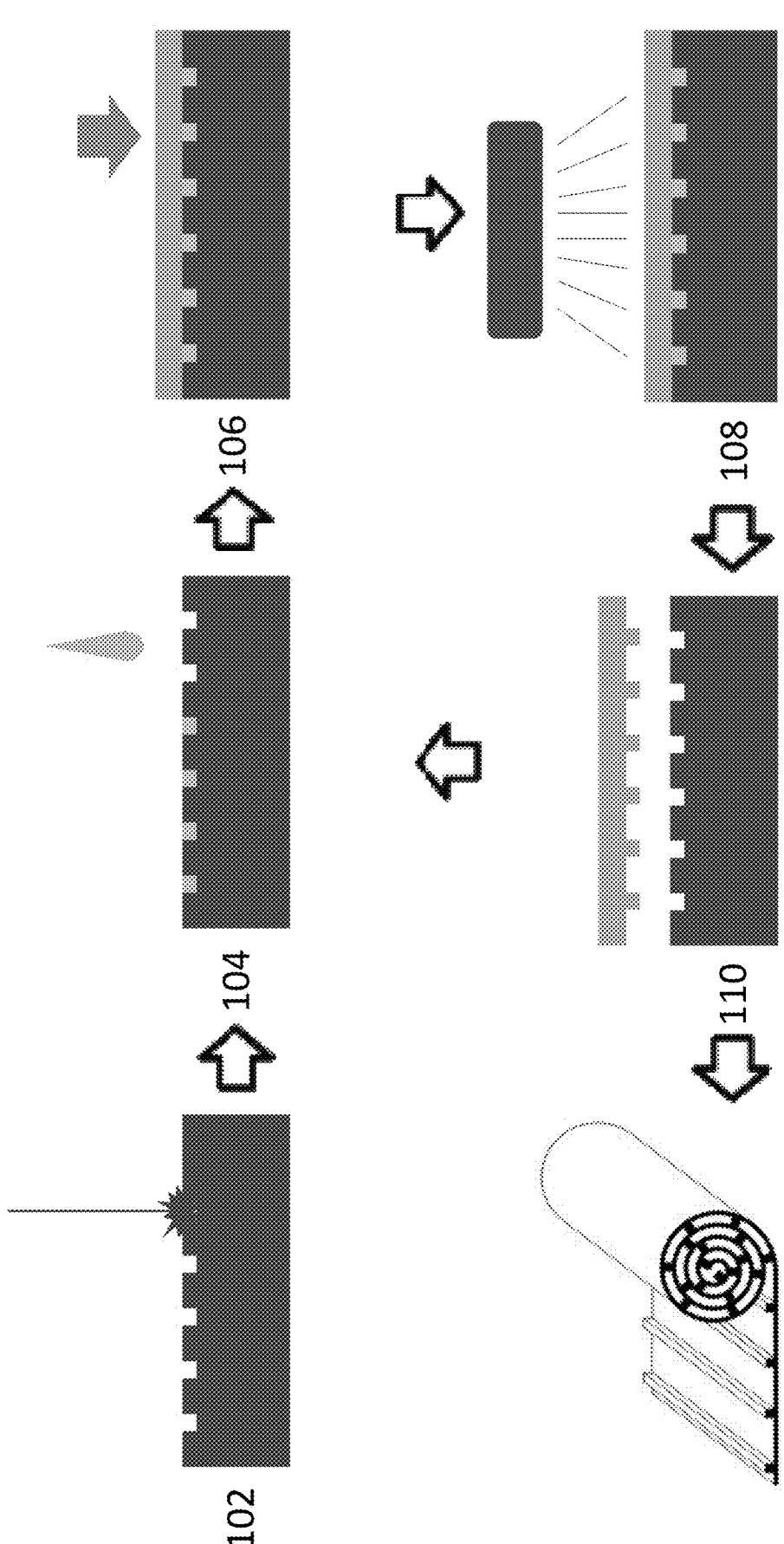
FIG. 6 is a schematic illustrating an exemplary method of fabricating rolled scaffolds.

The present invention also relates to methods of fabricating rolled scaffolds. Referring now to FIG. 5 and FIG. 6, an exemplary method 100 of fabricating a rolled scaffold is depicted. Method 100 begins with step 102, wherein a series of parallel grooves are etched into the top surface of a mold substrate. In step 104, a first material is deposited into each of the parallel grooves in the mold substrate. In step 106, a planar film is attached on top of the parallel grooves. In step 108, the first material is cured to the planar film to form a film with spacers. In step 110, the film with spacers is detached from the grooves on the mold substrate. In step 112, the film with spacers is rolled into a rolled scaffold.

The mold substrate material can be any suitable material that can be etched while also being able withstand any curing treatments, such as ultraviolet light or high temperature treatments. In some embodiments, the mold substrate material is silicone rubber. In some embodiments, the etched mold substrate is reusable, and can be reused after a simple cleaning, such as with a 70% ethanol wipedown. In some embodiments, the mold substrate can be attached to a roll, wherein the mold substrate can be rolled over an extremely long length of film and continuously receive new deposits of first material on one side of the roll while it cures deposits of first material to the film on the opposing side of the roll, allowing film with spacers to be made continuously and simultaneously in a roll-to-roll process.

The first material can be deposited or applied using any suitable means, including spin coating, dip coating, chemical vapor deposition, chemical solution deposition, physical vapor deposition, liquid bath immersion, and the like.

The first material and the planar film can be any suitable material that can support the growth of adherent cells. In some embodiments, the first and second materials can be selected from a polymer, including but not limited to: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate) (PVA), polyvinylhydroxide, poly(ethylene oxide) (PEO), polyorthoesters, and the like. In some embodiments, the first material and the planar film include the same material. In some embodiments, the first material is a UV-curable resin. In some embodiments, the planar film is polyethylene terephthalate.

The methods can further include any suitable method of attaching the spacer structures to a planar film. For example, in some embodiments, the rolled scaffolds can be constructed without the use of a mold substrate, such as by directly depositing the first material onto the planar film. Continuous or discontinuous thin lines of the first material can be deposited and solidified as appropriate for the material. For example, the first material can be extruded from one or more nozzles or printed, such as with a 3D printer, and UV-curable material can be cured by exposure to UV light while melted material can be solidified by cooling. As described above, the first material can be directly deposited onto the film in a continuous roll-to-roll process, wherein an extremely long length of film can have the first material deposited at an upstream location and can have the first material cured at a downstream location.

In some embodiments, the rolled scaffold can be subject to one or more surface treatments. The application of the one or more surface treatments can facilitate the adherence and growth of cell lines. For example, the one or more surface treatments can include one or more extracellular matrix material and/or blends of naturally occurring extracellular matrix material, including but not limited to collagen, fibrin, fibrinogen, thrombin, elastin, laminin, fibronectin, vitronectin, hyaluronic acid, chondroitin 4-sulfate, chondroitin 6-sulfate, dermatan sulfate, heparin sulfate, vixapatin (VP12), heparin, and keratan sulfate, proteoglycans, and combinations thereof. Some collagens that may be beneficial include but are not limited to collagen types I, II, III, IV, V, VI, VII, VIII, IX, X, XI, XII, XIII, XIV, XV, XVI, XVII, XVIII, and XIX. These proteins may be in any form, including but not limited to native and denatured forms. In various embodiments, the one or more surface treatments can include one or more carbohydrates such as chitin, chitosan, alginic acids, and alginates such as calcium alginate and sodium alginate. These materials may be isolated from plant products, humans or other organisms or cells or synthetically manufactured.

In various embodiments, the surface treatments can include natural peptides, such as glycyl-arginyl-glycyl-aspartyl-serine (GRGDS), arginylglycylaspartic acid (RGD), and amelogenin. In some embodiments, the surface treatments can include sucrose, fructose, cellulose, or mannitol. In some embodiments, the surface treatments can include nutrients, such as bovine serum albumin. In some embodiments, the surface treatments can include vitamins, such as vitamin B2, vitamin Ad, Vitamin D, Vitamin E, and Vitamin K. In some embodiments, the surface treatments can include nucleic acids, such as mRNA and DNA. In some embodiments, the surface treatments can include natural or synthetic steroids and hormones, such as dexamethasone, hydrocortisone, estrogens, and its derivatives. In some embodiments, the surface treatments can include growth factors, such as fibroblast growth factor (FGF), transforming growth factor beta (TGF-β), and epidermal growth factor (EGF). In some embodiments, the surface treatments can include a delivery vehicle, such as nanoparticles, microparticles, liposomes, viral and non-viral transfection systems.

In various embodiments, the surface treatments can include one or more therapeutics. The therapeutics can be natural or synthetic drugs, including but not limited to: analgesics, anesthetics, antifungals, antibiotics, anti-inflammatories, nonsteroidal anti-inflammatory drugs (NSAIDs), anthelmintics, antidotes, antiemetics, antihistamines, anticancer drugs, antihypertensives, antimalarials, antimicrobials, antipsychotics, antipyretics, antiseptics, antiarthritics, antituberculotics, antitussives, antivirals, cardioactive drugs, cathartics, chemotherapeutic agents, a colored or fluorescent imaging agent, corticoids (such as steroids), antidepressants, depressants, diagnostic aids, diuretics, enzymes, expectorants, hormones, hypnotics, minerals, nutritional supplements, parasympathomimetics, potassium supplements, radiation sensitizers, a radioisotope, fluorescent nanoparticles such as nanodiamonds, sedatives, sulfonamides, stimulants, sympathomimetics, tranquilizers, urinary anti-infectives, vasoconstrictors, vasodilators, vitamins, xanthine derivatives, and the like. The therapeutic agent may also be other small organic molecules, naturally isolated entities or their analogs, organometallic agents, chelated metals or metal salts, peptide-based drugs, or peptidic or non-peptidic receptor targeting or binding agents.

Rolled Scaffold Culture System

Figure 7:
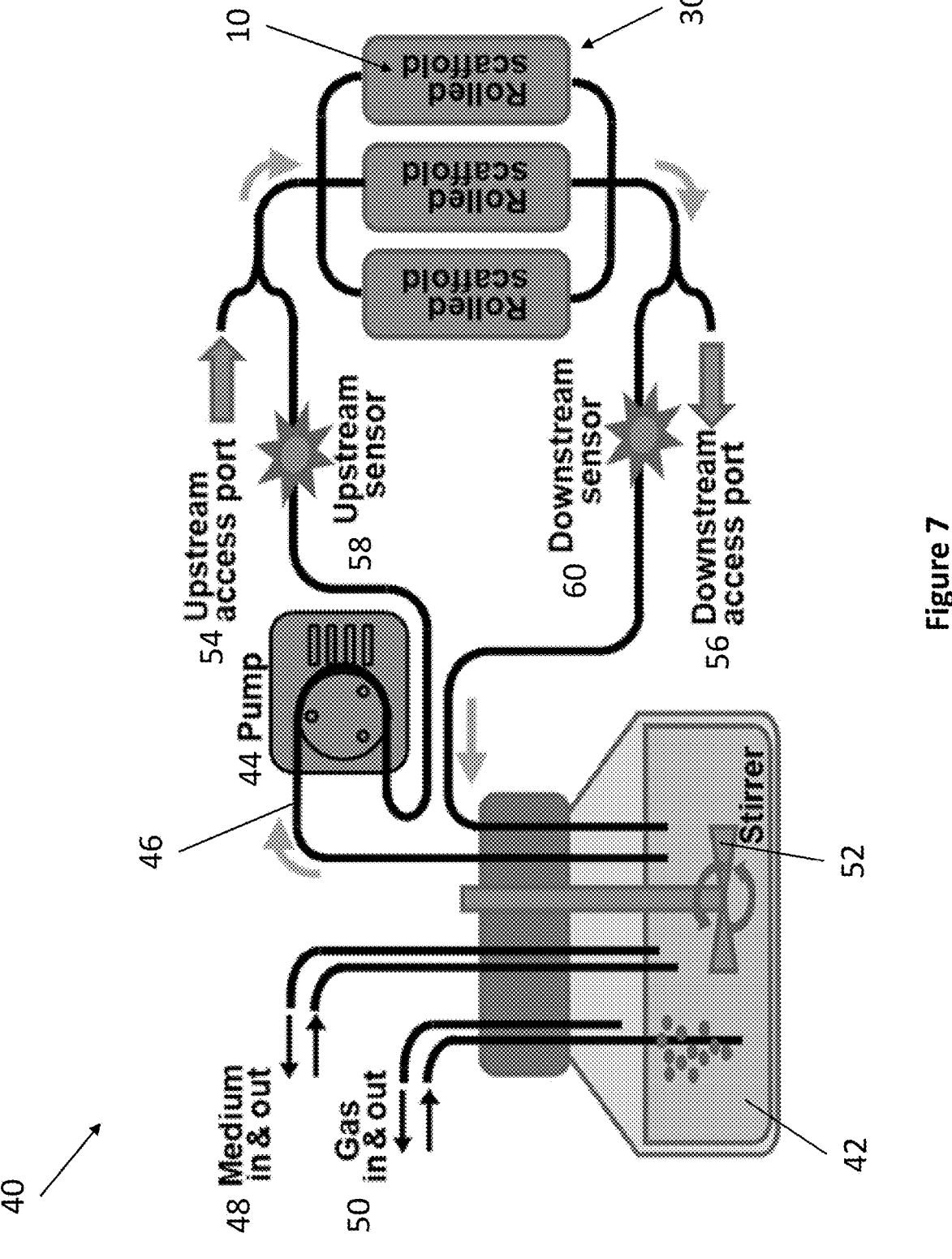
FIG. 7 depicts an exemplary cell culture system deploying three exemplary rolled scaffolds and holders.

The present invention also relates to systems for culturing and expanding adherent cells using the rolled scaffolds and rolled scaffold holders of the present invention. Referring now to FIG. 7, an exemplary cell culture system 40 is depicted. Culture system 40 comprises one or more reservoirs 42 connected to one or more rolled scaffolds 10, each in a holder 30, by tubing 46. The one or more rolled scaffolds 10, each within a holder 30, can be connected to the one or more reservoirs 42 in series, in parallel, or combinations thereof. Pump 44 is connected to tubing 46 to power the circulation of media between the one or more reservoirs 42 and the one or more rolled scaffolds 10. Tubing 46 can include any number of flow diverting mechanisms, such as stopcocks, valves, and other fluidic devices, such that the circulation of media can be directed in any desired fashion. In some embodiments, reservoir 42 can also be connected to one or more media sources 48, one or more gas sources 50, one or more chemical reagent sources, and combinations thereof, wherein connected sources each provide a fresh supply to the one or more reservoirs 42. Each reservoir 42 can further comprise a stirring impeller 52 to mix the contents of the one or more reservoirs 42.

In some embodiments, tubing 46 can comprise one or more access ports 54 upstream from the rolled scaffolds 10, one or more access ports 56 downstream from the rolled scaffolds, or both. The upstream access port 54 can be used to introduce any desired content into the media circulation path. Exemplary content includes cells, nucleic acid molecules, DNA, RNA, peptides, proteins, small molecules, dyes, hormones, vitamins, growth factors, stem cell factors, and the like. The downstream access port 56 can be used to capture samples of media flowing out of the rolled scaffolds 10 or to collect harvested cells from the rolled scaffolds 10. In some embodiments, tubing 46 can comprise one or more sensors 58 upstream from the rolled scaffolds 10 and one or more sensors 60 downstream from the rolled scaffolds 10. The sensors 58 and 60 can be any desired sensor, including but not limited to: temperature sensors, flow sensors, pH sensors, gas concentration sensors, analyte sensors, and the like.

Cells can be cultured onto the rolled scaffolds 10 prior to being connected to system 40. Cells can also be introduced into system 40, such as through the one or more upstream access ports 54. The circulation of media can be temporarily halted, either by stopping pump 44 or closing a stopcock or valve downstream from the rolled scaffold holders 30, to permit the cells to adhere to the rolled scaffolds 10. Once the cells have adhered, pump 44 can be restarted or the stopcocks or valves can be reopened to restart circulation of media. The cells can be removed from the rolled scaffolds 10 by the application of any suitable cell dissociation solution. In some embodiments, the cells can be removed after removing the rolled scaffolds 10 from system 40. In other embodiments, the cells can be removed by introducing a cell dissociation solution through the one or more upstream access ports 54. As described above, the circulation of media can be temporarily halted to permit the cell dissociation solution to detach the adhered cells from the rolled scaffolds 10 within the holders 20. Once the cells have detached, circulation can be restarted, and the cells can be retrieved through the one or more downstream access ports 56.

The hydrodynamic shear stress and the mass transfer rate in the rolled scaffold is precisely controllable and highly uniform, increasing the uniformity and repeatability of stem cell production. The shear stress ($\tau$) on the internal surface of the rolled scaffold is $\tau = -(12Q\mu h^{-2}w^{-1})$, wherein Q is flow rate of media, $\mu$ is dynamic viscosity of the media, h is the height of the rolled scaffold channel, and w is the width of the rolled scaffold channel (Lu H et al., Analytical chemistry, 2004, 76(18):5257-5264). As each channel in the rolled scaffold has the same height, the media flow generates highly uniform shear stress. A wide range of shear stress can be produced by varying flow rate Q, as shown in Table 2.

TABLE 2

| | Shear stress (dyn/cm$^2$) | Media refresh time (min) | Max variation in dissolved oxygen* | Flow rate (mL/min) |
|---|---|---|---|---|
| Minimum flow | 0.15 | 4.5 | 10% | 33 |
| High flow | 20 | 0.03 | 0.08% | 4400 |

The shear stress can be varied by changing the flow rate. This table is based on the large-sized rolled scaffold in Table 1. (*A fully confluent cell layer with 10$^5$ cells/cm$^2$ and the oxygen consumption rate in the literature are assumed).

The minimum flow rate is conservatively set as the flow rate that will cause 10% decrease in the dissolved oxygen (dO) concentration downstream of the rolled scaffold with confluent culture. The shear stress produced by the minimum flow is one-order of magnitude lower than other cell expansion platforms (1-5 dyn/cm$^2$) (Cormier J T et al., Tissue engineering, 2006, 12(11):3233-3245; Youn B S et al., Biotechnology progress, 2005, 21(3):984-993; Badenes S M et al., PloS one, 2016, 11(3):e0151264; Wang Y et al., Stem cell research, 2013, 11(3):1103-1116; Kehoe D E et al., Tissue Engineering Part A, 2009, 16(2):405-421). The decrease in the oxygen concentration with the minimum flow will be less than 10% with non-confluent cell layers and can be further reduced by increasing the channel height or the flow rate. By increasing flowrate, shear stress can be increased up to 20 dyn/cm$^2$, which is above the shear stress used to induce endothelial differentiation, so that the maturation of iPSC (induced pluripotent stem cells)-derived EPC (epithelial cells) can be facilitated with mechanical stimuli (Adams W J et al., The FASEB Journal, 2013, Supplement 27(1):379.1; Cui X et al., Biochemical and biophysical research communications, 2012, 425(2):419-425; Wolfe R P et al., Biotechnology and bioengineering, 2013, 110(4): 1231-1242; Yamamoto K et al., American Journal of Physiology-Heart and Circulatory Physiology, 2005, 288(4): H1915-H1924).

The microenvironment is not affected by the increased capacity of culture. In suspension cultures with stirred bioreactors, increasing capacity leads to a decrease in the surface-area-to-volume ratio of the cell suspension and eventually leads to increased mechanical agitation and hydrodynamic shear stress. On the other hand, the culture capacity of the rolled scaffold is increased by increasing the number of identical channels without changing their geometry. Hence, the microenvironment of the rolled scaffold is independent of the culture capacity.

The rolled scaffold setup is modular for quick culture scale-out and is easy to operate. As described above, the setup of the rolled scaffold is shown in FIG. 7. The reservoir can have a gas inlet/outlet and a stirring impeller for gas exchange of culture medium, as well as a medium inlet/outlet for media perfusion. The culture medium can be pumped into the rolled scaffolds by a peristaltic pump. Multiple rolled scaffolds can be attached in parallel for a larger capacity in a reconfigurable manner. The upstream and downstream sensor modules can be used to measure any number of parameters, including pH, dO, and the presence and amount of any number of analytes, including glucose and lactate.

Global metabolic activities of cells can be easily monitored in real time by comparing the measurements from the upstream and downstream sensors. The upstream access port can be used to inject cell suspensions for seeding and cell dissociation solution for harvesting, whereas the downstream access port is used to collect the harvested cells. The entire setup can be placed in an incubator, such as at 37° C. and 5% CO$_2$.

The medium in the reservoir can be stirred and aerated vigorously without fear of damaging the cells, as the media reservoir and the rolled scaffolds are separated. Therefore, the rolled scaffolds can support larger cell populations with lesser amounts of medium. Existing protocols for 2D culture can be easily adopted, as the cells grow in monolayers in the rolled scaffolds. The media in the rolled scaffolds can be changed fast and efficiently while maintaining laminar flow with a low Reynold's number. This feature enhances transportation of gases and nutrients to cells, as well as preventing the build-up of metabolic byproducts and pH decreases, which can reduce cell proliferation and pluripotency. Rapid exchange of media in the rolled scaffolds also facilitates seeding and harvesting. The rolled scaffolds can also be affordably mass-produced with a highly matured roll-to-roll process (Ahn S H et al., Advanced materials, 2008, 20(11): 2044-2049; Kooy N et al., Nanoscale research letters, 2014, 9(1):320).

The cells that can be cultured using the rolled scaffolds of the present invention can be any suitable cell. For example, in some embodiments, the rolled scaffolds of the present invention can be used to culture recombinant cells to produce biopharmaceutical products, including therapeutic proteins and monoclonal antibodies. In some embodiments the cells can include progenitor cells, pluripotent cells, stem cells, other differentiable cells, and the like. In some embodiments, the rolled scaffolds of the present invention direct differentiation of progenitor cells and/or stem cells. In some embodiments, the rolled scaffolds of the present invention direct and maintain phenotype plasticity of the cells that are seeded therein. In some embodiments, the rolled scaffolds of the present invention are used to support niche expansion of stem cells seeded therein.

In some embodiments, the compositions and methods useful with the present invention enhance the culturing of cells, for example, differentiable cells such as induced pluripotent stem cells, embryonic stems cells, hematopoietic stem cells, adipose derived stem cells, bone marrow derived stem cells and the like. In some embodiments, the differentiatable cells are directed to differentiate into cells of target tissues, for example fibroblasts, osteocytes, epithelial cells, cardiomyocytes, endothelial cells, myocytes, neurocytes, and the like. In some embodiments, at different points during culturing the differentiable cells, various components may be added to the cell culture such that the medium can contain components such as growth factors, differentiation factors, and the like other than those described herein.

In some embodiments, the compositions and methods can comprise a basal salt nutrient solution. A basal salt nutrient solution refers to a mixture of salts that provide cells with water and certain bulk inorganic ions essential for normal cell metabolism, maintain intra- and extra-cellular osmotic balance, provide a carbohydrate as an energy source, and provide a buffering system to maintain the medium within the physiological pH range. For example, basal salt nutrient solutions may include, but are not limited to, Dulbecco's Modified Eagle's Medium (DMEM), Minimal Essential Medium (MEM), Basal Medium Eagle (BME), RPM1 1640, Hams F-10, Ham's F-12, β-Minimal Essential Medium (β-MEM), Glasgow's Minimal Essential Medium (G-MEM), and Iscove's Modified Dulbecco's Medium, and mixtures thereof. In some embodiments, the basal salt nutrient solution is an approximately 50:50 mixture of DMEM and Ham's F12.

In some embodiments, the compositions and methods useful with the present invention provide for one or more soluble attachment factors or agents, such as soluble attachment components as contained in the human serum, which at the appropriate concentration range facilitates cell attachment to tissue culture type plastic and or the surface of the rolled scaffold. Such cell attachment allows cells to attach and form a monolayer but in the absence of a feeder layer or a substrate coating, e.g., a matrix coating, Matrigel, and the like. In some embodiments, human serum is utilized in order to provide an animal-free environment. In some embodiments, serum from animal sources, for example goat, calf, bovine, horse, mouse, and the like is utilized. Serum can be obtained from any commercial supplier of tissue culture products, examples include Gibco-Invitrogen Corporation (Grand Island, N.Y. USA), Sigma (St. Louis Mo., USA) and the ATCC (Manassas, Va. USA). The serum used may be provided at a concentration range of about 0.1% to about 20%, about 5% to about 15%, about 7% to about 12%, about 10%, 0.1 to about 3%, about 0.5 to about 2%, about 0.5 to about 1.5%, and about 0.5 to about 1%.

In some embodiments, as contemplated herein, the cells on the rolled scaffolds can be passaged using enzymatic, non-enzymatic, or manual dissociation methods prior to and/or after contact with a defined medium. Non-limiting examples of enzymatic dissociation methods include the use of proteases such as trypsin, collagenase, dispase, and accutase (marine-origin enzyme with proteolytic and collagenolytic enzymes in phosphate buffered saline; Life Technologies, Carlsbad, Calif.). In some embodiments, accutase is used to passage the contacted cells. When enzymatic passaging methods are used, the resultant culture can comprise a mixture of singlets, doublets, triplets, and clumps of cells that vary in size depending on the enzyme used. A non-limiting example of a non-enzymatic dissociation method is a cell dispersal buffer. Manual passaging techniques have been well described in the art, such as in Schulz et al., 2004 Stem Cells, 22(7):1218-38. The choice of passaging method is influenced by other culture conditions, including but not limited to feeders and/or extracellular matrices.

In some embodiments, the methods described herein allow for expansion of cells, followed by detaching the cells from the rolled scaffolds and passaging of the detached cells on the rolled scaffolds or similar cell culture devices, so that the cells retain their characteristics such as pluripotency through expansion and serial passages. In addition, the methods of expansion and passage described herein are carried out in a closed system which ensures sterility during the production process.

Methods of inducing differentiation are known in the art and can be employed to induce the desired stem cells to give rise to cells having a mesodermal, ectodermal or endodermal lineage.

After culturing the stem cells in a differentiating-inducing medium for a suitable time (e.g., several days to a week or more), the stem cells can be assayed to determine whether, in fact, they have acquired the desired lineage.

Methods to characterize differentiated cells that develop from the stem cells of the invention, include, but are not limited to, histological, morphological, biochemical and immunohistochemical methods, or using cell surface markers, or genetically or molecularly, or by identifying factors secreted by the differentiated cell, and by the inductive qualities of the differentiated stem cells.

In another embodiment, the cells can be genetically modified, e.g., to express exogenous (e.g., introduced) genes ("transgenes") or to repress the expression of endogenous genes, and the invention provides a method of genetically modifying such cells and populations. In accordance with this method, the cells are exposed to a gene transfer vector comprising a nucleic acid including a transgene, such that the nucleic acid is introduced into the cell under conditions appropriate for the transgene to be expressed within the cell. The transgene generally is an expression cassette, including a polynucleotide operably linked to a suitable promoter. The polynucleotide can encode a protein, or it can encode biologically active RNA (e.g., antisense RNA or a ribozyme).

The expression cassette containing the transgene should be incorporated into a genetic vector suitable for delivering the transgene to the cells. Depending on the desired end application, any such vector can be so employed to genetically modify the cells (e.g., plasmids, naked DNA, viruses such as adenovirus, adeno-associated virus, herpesviruses, lentiviruses, papillomaviruses, retroviruses, etc.). Any method of constructing the desired expression cassette within such vectors can be employed, many of which are well known in the art (e.g., direct cloning, homologous recombination, etc.). Of course, the choice of vector will largely determine the method used to introduce the vector into the cells (e.g., by protoplast fusion, calcium-phosphate precipitation, gene gun, electroporation, infection with viral vectors, etc.), which are generally known in the art.

The genetically altered cells can be employed to produce the product of the transgene. In other embodiments, the genetically modified cells are employed to deliver the transgene and its product to an animal. For example, the cells, once genetically modified, can be introduced into the animal under conditions sufficient for the transgene to be expressed in vivo.

In other embodiments, cells can be employed as therapeutic agents, for example in cell therapy applications. Generally, such methods involve transferring the cells to desired tissue, either in vitro (e.g., as a graft prior to implantation or engrafting) or in vivo, to animal tissue directly. The cells can be transferred to the desired tissue by any method appropriate, which generally will vary according to the tissue type. For example, cells can be transferred to a graft by bathing the graft (or infusing it) with culture medium containing the cells. Alternatively, the cells can be seeded onto the desired site within the tissue to establish a population. Cells can be transferred to sites in vivo using devices such as catheters, trocars, cannulae, stents (which can be seeded with the cells), etc.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention, and are not to be construed as limiting in any way the remainder of the disclosure.

Example 1: Rolled Scaffold Platform for Large-Scale Cell Culture

The following study demonstrates rolled scaffolds as a viable platform for large-scale cell culture. The rolled scaffold in this example is a thin polyethylene terephthalate (PET) film with spacers and is rolled into a cylinder with a predetermined gap between each turn. The rolled scaffold has numerous channels enclosed by the film and the spacers. Adherent cells grow and differentiate as monolayers on the inner surface of these channels in the rolled scaffold. The fabrication process of rolled scaffolds is presented, followed by the expansion of Chinese Hamster Ovary (CHO) cells with the rolled scaffolds.

Fabrication and Demonstration of the Rolled Scaffold

Figure 8A:
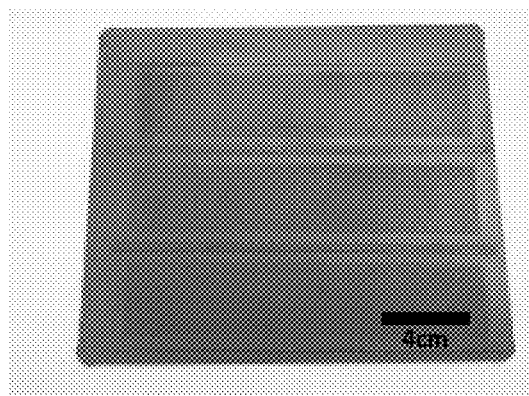
FIG. 8A through FIG. 8E depict prototype rolled scaffolds.
Figure 8B:
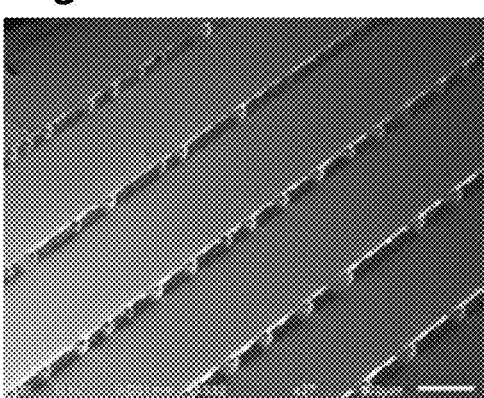
Figure 8C:
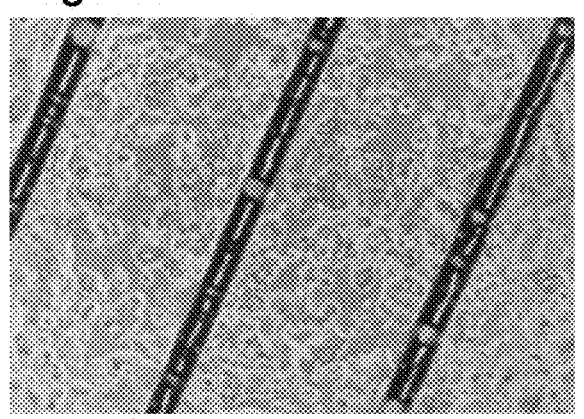
Figure 8D:
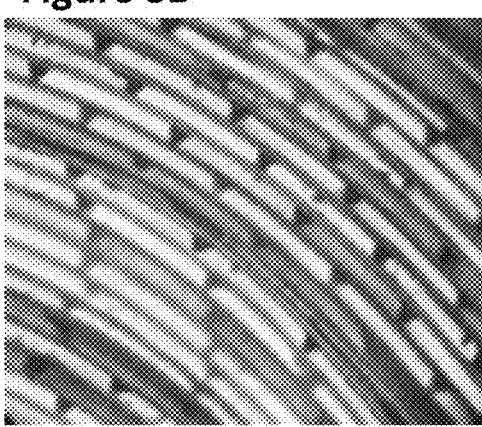
Figure 8E:
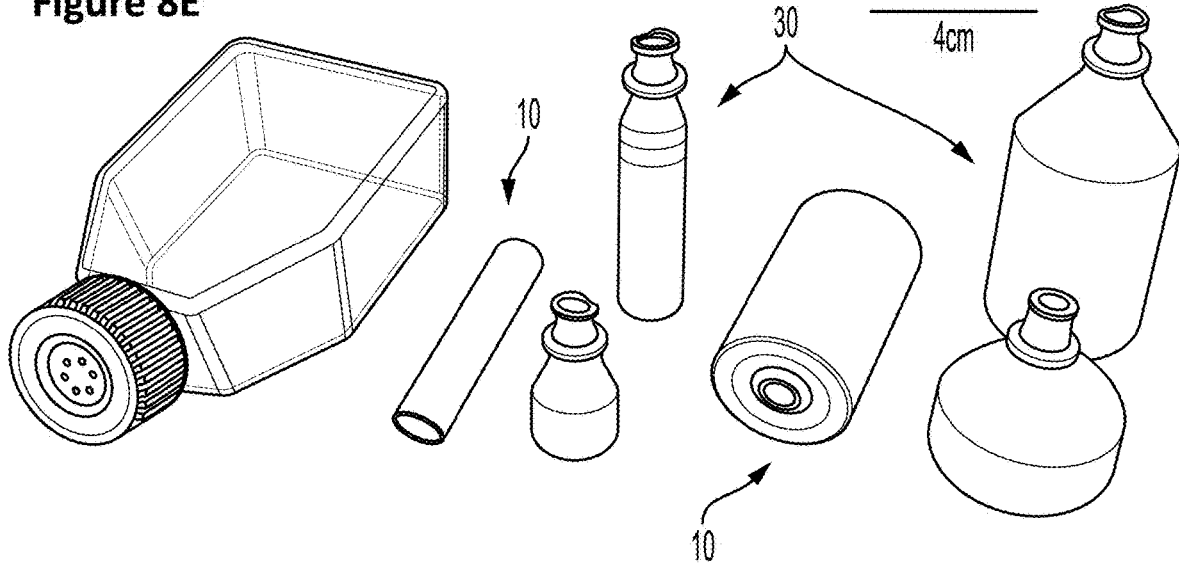

The fabrication process of the rolled scaffold with a planar mold is shown in FIG. 6. The patterns of the spacers are engraved on a silicone rubber film with a laser engraver. UV resin (1187-M, Dymax, USA) is applied on the silicone mold and PET film (polyethylene terephthalate, 50 μm thick, Tekra, USA) is attached. The UV resin is cured by 395 nm UV light and the film is detached with the cured UV resin spacers. Individual strips of the plastic film with the spacers can be connected into a single strip and rolled into a rolled scaffold. The completed rolled scaffold is packaged in a 3D-printed rolled scaffold holder. The silicone mold can be reused after cleaning with 70% ethanol. FIG. 8A shows the silicone mold (28 cm×22 cm) that can process three strips (22 cm×4 cm) of plastic film at the same time. It typically takes about 3 hours to make a medium rolled scaffold and about 30 min to make a small rolled scaffold. The production of one large rolled scaffold using this approach is estimated to take about 20 hours.

Rolled Scaffold Platform

Figures 9A, 9B:
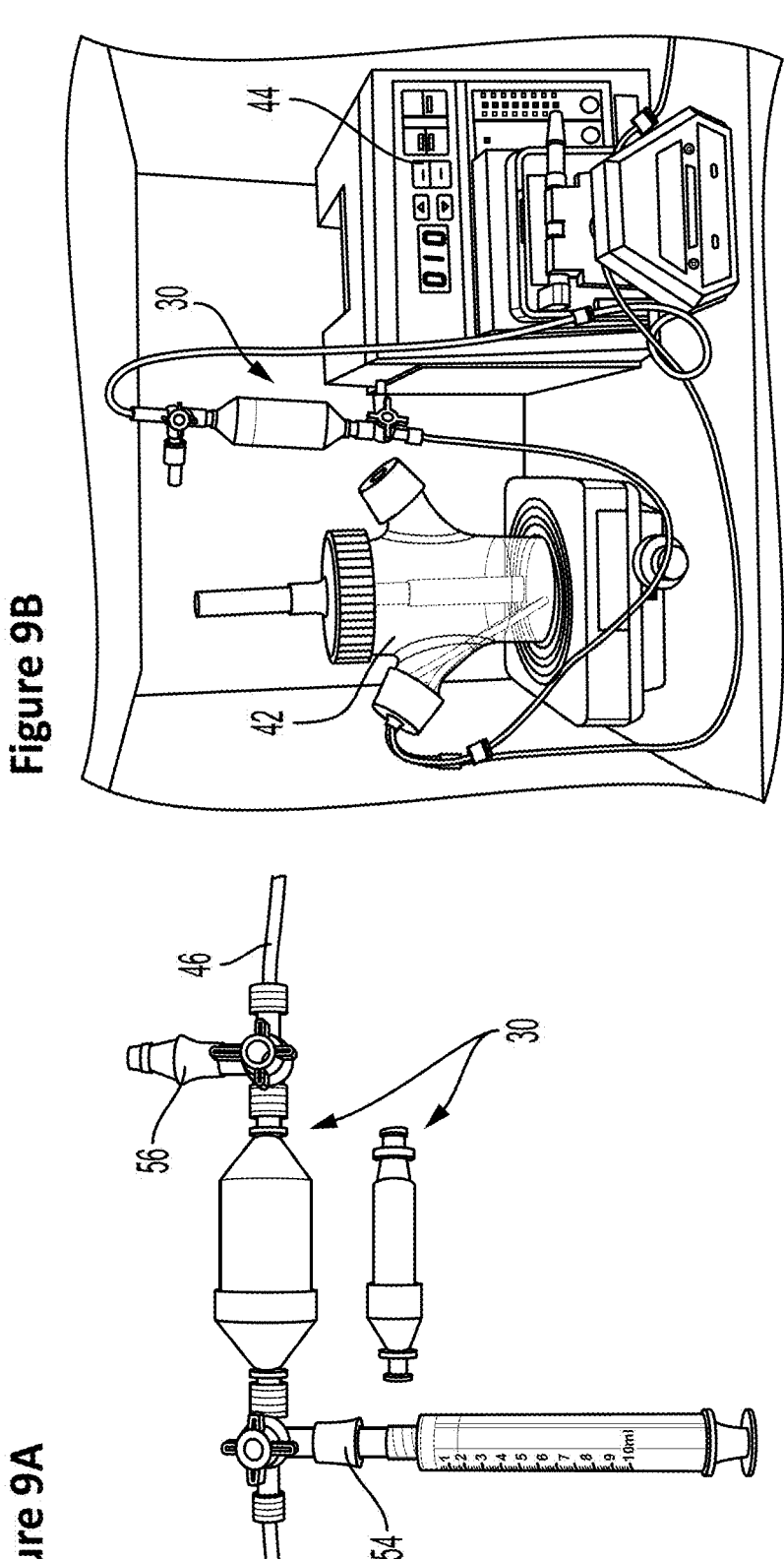
FIG. 9A and FIG. 9B depict prototype cell culture systems.

The schematic diagram of the rolled scaffold culture platform is shown in FIG. 7, and the developed setup is shown in FIG. 9A and FIG. 9B. In FIG. 9A, the rolled scaffold is inserted into a rolled scaffold holder, which is then connected between two stopcocks. Each stopcock controls the connection of the rolled scaffold to the reservoir and the upstream or downstream access port. On the upstream and downstream access ports, needle-free sterile luer lock connectors (Clave, Victus, Inc., US) are used for aseptic injection and sampling of fluid. A peristaltic pump is used to flow media from the reservoir and the reservoir is stirred for uniform gas exchange of the media. The upstream and downstream sensor modules are not implemented in FIG. 9A. The sensor modules can be located before and after the three-way stopcocks. The entire setup can be retained in a 37° C. 5% $CO_2$ incubator, as shown in FIG. 9B.

Culture Protocol

The rolled scaffolds can be sterilized by autoclaving. Cells can be easily seeded and harvested with the use of the upstream and downstream access ports. To seed, a cell suspension can be injected into the rolled scaffold through the upstream access port. The flow is stopped for cell attachment by closing two stopcocks. After cell attachment, growth medium is used to flush unattached cells in the rolled scaffold. Growth media may then be flowed through the rolled scaffold for normal operation. Cells can be harvested using a similar procedure by adding cell dissociation reagent through the upstream access port and stopping the flow. Detached cells may be collected at the downstream port by flowing growth media through the rolled scaffold.

Expansion of CHO cells

Figure 10A:
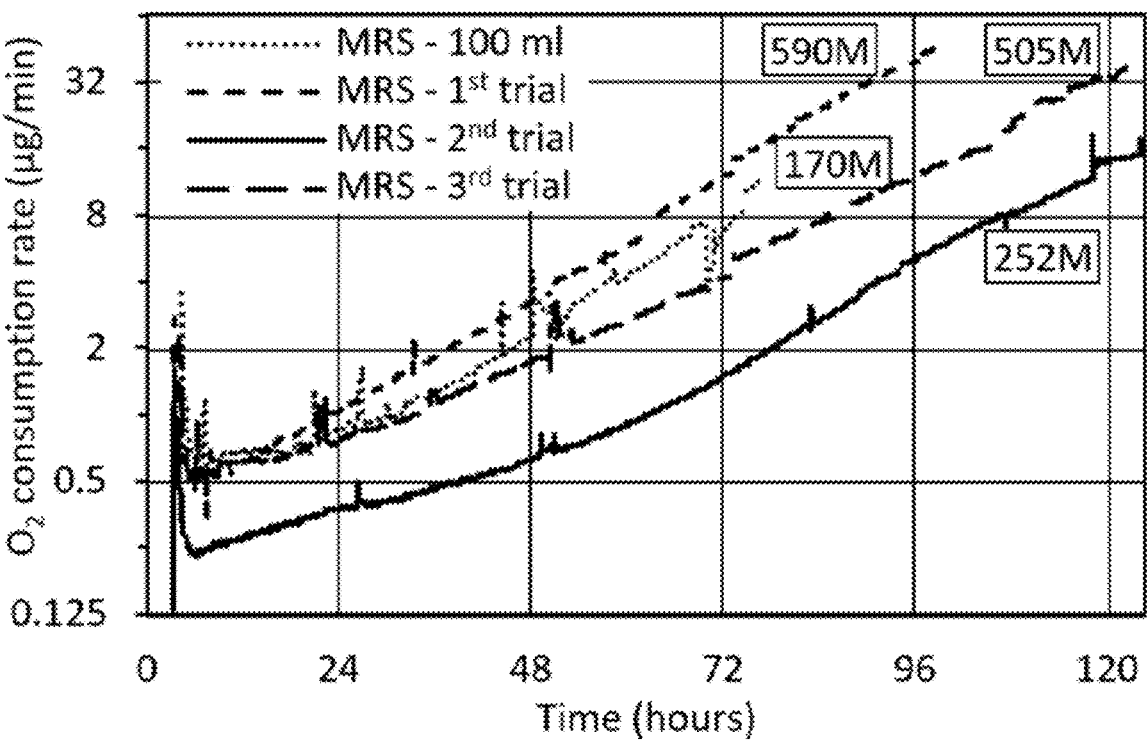
FIG. 10A and FIG. 10B depict the results of culturing Chinese Hamster Ovary (CHO) cells using rolled scaffolds.
Figure 10B:
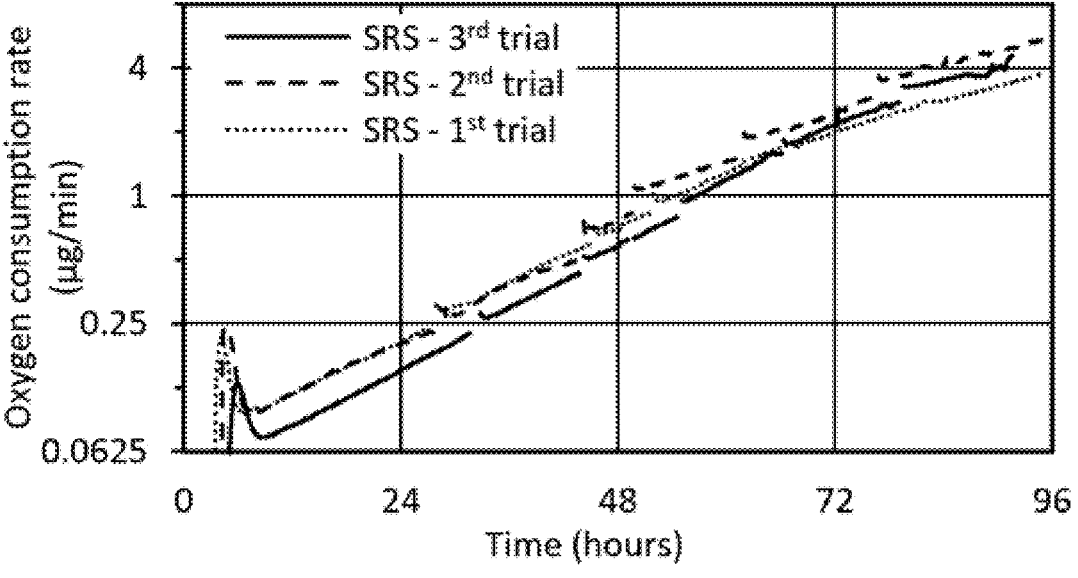

CHO cells and mouse embryonic stem cells were expanded using small and medium rolled scaffolds, as described in Table 1. 40±4 million CHO cells were produced in a small rolled scaffold using 100 mL of growth media and up to 590 million CHO cells were produced in a medium rolled scaffold using 1000 mL of growth media. The number of cells was obtained by detaching the cells from the rolled scaffold at the end of the culture with trypsin and counting. Oxygen consumption in the rolled scaffold was measured to monitor the growth of the cells in real time, as shown in FIG. 10A and FIG. 10B. The cells showed a stable exponential growth up to 4 days for small and medium rolled scaffolds. In both rolled scaffolds, the doubling time of CHO cells was 14.6±0.52 hours.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A rolled scaffold comprising:
   a planar film having an upper surface, a lower surface, a length, and a width;
   a plurality of elongate spacers attached to one of the surfaces, the spacers having a height, a width, and a length that spans the entire width of the film;
   wherein the film is rollable along its length into a cylindrical shape such that the plurality of elongate spacers face and press against the opposing surface of the rolled film, and wherein the height of the plurality of elongate spacers maintain a space between the rolled film layers, wherein the plurality of elongate spacers are set apart at intervals to form discrete channels; and
   a casing having a hollow interior sized to encase the rolled scaffold, wherein the casing is formed from a first and a second endcap connectable at a junction, wherein the first endcap and the second endcap respectively comprise a first tapered opening and a second tapered opening, wherein the first and second tapered openings are in fluid communication with the hollow interior and are capable of passing at least one fluid through the rolled scaffold.

2. The rolled scaffold of claim 1, wherein the plurality of elongate spacers have a cross-sectional shape selected from the group consisting of: a square, a rectangle, a trapezoid, a triangle, a circle segment, and an ovoid segment.

3. The rolled scaffold of claim 1, wherein the plurality of elongate spacers have one or more discontinuities.

4. A method of culturing cells, the method comprising the steps of:
   providing the rolled scaffold of claim 1;
   attaching at least one cell to at least one surface of the rolled scaffold; and
   administering nutrients and oxygen to the at least one cell by applying a flow of culture media through the rolled scaffold along its length.

5. A rolled scaffold comprising:
   a planar film having an upper surface, a lower surface, a length, and a width;
   a plurality of elongate spacers attached to one of the surfaces, wherein the plurality of elongate spacers have a height, a width, and a length that spans the entire width of the film, wherein the film is rollable along its length into a cylindrical shape such that the plurality of elongate spacers face and press against the opposing surface of the rolled film, wherein the height of the plurality of elongate spacers maintain a space between the rolled film layers, wherein the plurality of elongate spacers are set apart at intervals to form discrete channels; and a casing having a hollow interior sized to encase the rolled scaffold, wherein the casing is formed from a first and a second endcap connectable at a junction, wherein the first endcap and the second endcap respectively comprise a first tapered opening and a second tapered opening, wherein the first and second opening are aligned along a longitudinal central axis of the rolled scaffold, wherein the first and second tapered opening are in fluid communication with the hollow interior and are capable of passing at least one fluid directly along the path of the longitudinal central axis and through the rolled scaffold.

6. A rolled scaffold comprising:

a planar film having an upper surface, a lower surface, a length, and a width;

a plurality of elongate spacers attached to one of the surfaces, wherein the plurality of elongate spacers have a height, a width, and a length that spans the entire width of the film, wherein the plurality of elongate spacers comprise ultraviolet curing material, wherein the plurality of elongate spacers are cured with ultraviolet light onto the planar film, wherein the film is rollable along its length into a cylindrical shape such that the plurality of elongate spacers face and press against the opposing surface of the rolled film, wherein the height of the plurality of elongate spacers maintain a space between the rolled film layers, wherein the plurality of elongate spacers are set apart at intervals to form discrete channels; and a casing having a hollow interior sized to encase the rolled scaffold, wherein the casing is formed from a first and a second endcap connectable at a junction, wherein the first endcap and the second endcap respectively comprise a first tapered opening and a second tapered opening, wherein the first and second opening are aligned along a longitudinal central axis of the rolled scaffold, wherein the first and second tapered opening are in fluid communication with the hollow interior and are capable of passing at least one fluid directly along the path of the longitudinal central axis and through the rolled scaffold.

* * * * *